United States Patent
Starkenmann et al.

(10) Patent No.: US 12,239,151 B2
(45) Date of Patent: Mar. 4, 2025

(54) 2-ACETYLPYRROLINE PRECURSOR

(71) Applicant: FIRMENICH SA, Satigny (CH)

(72) Inventors: Christian Starkenmann, Satigny (CH); Yvan Niclass, Satigny (CH)

(73) Assignee: FIRMENICH SA, Satigny (CH)

( * ) Notice: Subject to any disclaimer, the term of this patent is extended or adjusted under 35 U.S.C. 154(b) by 505 days.

(21) Appl. No.: 17/621,825

(22) PCT Filed: Aug. 6, 2020

(86) PCT No.: PCT/EP2020/072139
§ 371 (c)(1),
(2) Date: Dec. 22, 2021

(87) PCT Pub. No.: WO2021/023818
PCT Pub. Date: Feb. 11, 2021

(65) Prior Publication Data
US 2022/0361542 A1 Nov. 17, 2022

(30) Foreign Application Priority Data
Aug. 8, 2019 (EP) .................................... 19190645

(51) Int. Cl.
A23L 27/20 (2016.01)
C07D 207/08 (2006.01)

(52) U.S. Cl.
CPC ........ *A23L 27/2054* (2016.08); *C07D 207/08* (2013.01); *A23V 2002/00* (2013.01)

(58) Field of Classification Search
CPC .................... A23L 27/2054; C07D 207/08
See application file for complete search history.

(56) References Cited

FOREIGN PATENT DOCUMENTS

| CN | 105265960 A | * | 1/2016 |
| CN | 106036607 A | * | 10/2016 |

(Continued)

OTHER PUBLICATIONS

Starkenmann, "Occurrence of 2-Acetyl-1-pyrroline and Its Non-volatile Precursors in Celtuce (*Lactuca sativa* L. var. *augustana*), Journal of Agricultural Food Chemistry", 2019, 67, 11710-11717 (Year: 2019).*

(Continued)

*Primary Examiner* — Changqing Li
(74) *Attorney, Agent, or Firm* — Armstrong Teasdale LLP

(57) ABSTRACT

Described herein is a precursor compound of formula (I) releasing 2-acetyl-1-pyrroline and a method to release 2-acetyl-1-pyrroline from the precursor compound of formula (I)

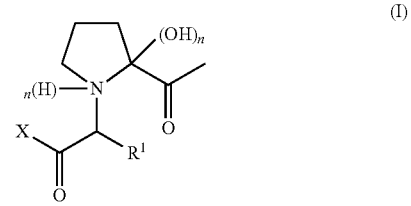

in the form of any one of its stereoisomers, tautomers, salts or as a mixture thereof, where $R^1$ represents a hydrogen atom or a $C_1$ to $C_{10}$ hydrocarbon group optionally including one to three heteroatoms; X represents an amino acid, a peptide or a $OR^2$ wherein $R^2$ represents a hydrogen atom or a $C_1$ to $C_{20}$ hydrocarbon group optionally including one to (Continued)

three heteroatoms and n is 0 when the dotted line represents a single bond or n is 1 when the dotted line represents no bond.

8 Claims, 1 Drawing Sheet

(56) References Cited

FOREIGN PATENT DOCUMENTS

| CN | 108271858 A | * | 7/2018 |
|---|---|---|---|
| WO | 2009034528 A1 | | 3/2009 |
| WO | 2010136778 A1 | | 12/2010 |
| WO | 2011006080 A2 | | 1/2011 |

OTHER PUBLICATIONS

Adams, "Structure of monocrotaline. IX. Proof of the position of the double bond in retronecine", JACS, 1943,65, pp. 2009-2012 (Year: 1943).*

Adams, "The Absolute Configuration of the C8-Atom in the Pyrrolizidine Moieties of the Senecio Alkaloids", JACS, 1959,81, pp. 5803-5805 (Year: 1959).*

International Search Report and Written Opinion for international application PCT/EP2020/072139; Aug. 13, 2020; 14 pages.

Al-Awadi et al., "Kinetics and mechanism of thermal gas-phase elimination of α-substituted carboxylic acids: role of relative basicity of α-substituents and acidity of incipient proton", Journal of Physical Organic Chemistry, 2000, pp. 499-504, 13.

* cited by examiner

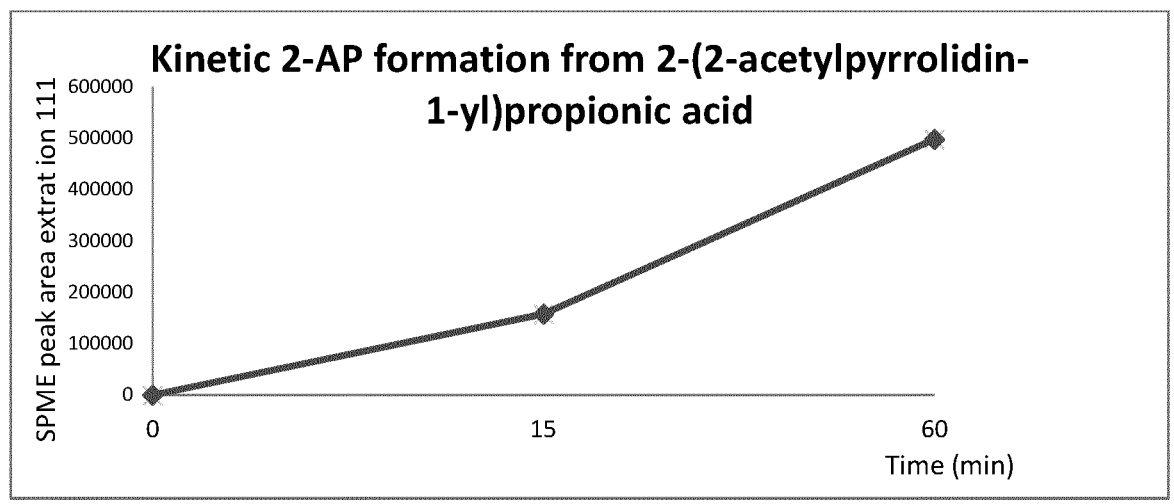

2-ACETYLPYRROLINE PRECURSOR

CROSS-REFERENCE TO RELATED APPLICATIONS

This application is a U.S. National Phase Application of International Patent Application No. PCT/EP2020/072139, filed Aug. 6, 2020, which claims priority to European Patent Application No. 19190645.2, filed Aug. 8, 2019, the entire contents of which are hereby incorporated by reference herein.

TECHNICAL FIELD

The present invention relates to the field of flavor. More particularly, it concerns a precursor compound of formula (I) releasing 2-acetyl-1-pyrroline and a method to release 2-acetyl-1-pyrroline from the precursor compound of formula (I). Moreover, the present invention relates to a flavoring composition and a flavored consumer product comprising at least one compound of formula (I).

BACKGROUND OF THE INVENTION

Some of the most sought ingredients in the flavor industry are the ones imparting a rice/basmati impression. 2-acetyl-1-pyrroline (2-AP) was identified as the principal aroma compound responsible for the pleasant aroma in scented rice while possessing a bread, nutty, popcorn and basmati notes. Moreover, the scope of 2-AP expands beyond rice as it reveals its presence in a large variety of living systems and food products and imparts organoleptic impression needed in a large amount of flavored article.

However, 2-AP is highly unstable due to the pyrroline ring rendering the use of said compound in flavored article very difficult.

So, there is a need to develop a mean to stabilize 2-AP allowing to release the desired flavor during the food preparation, e.g. through the action of heat or pH modification.

The present invention provides new compounds able to release 2-AP to improve the consumer experience under certain triggers.

SUMMARY OF THE INVENTION

Surprisingly, it has now been discovered that the precursor compound of formula (I) allows stabilizing 2-acetyl-1-pyrroline by releasing it when needed in the consumer product article. The present invention's allows to improve the organoleptic impact of 2-acetyl-1-pyrroline by avoiding premature decomposition in flavoring compositions or flavored consumer products.

So, the first object of the present invention is method to release 2-acetyl-1-pyrroline from a precursor compound of formula

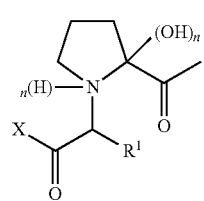

(I)

in the form of any one of its stereoisomers, tautomers, salts or as a mixture thereof, and wherein $R^1$ represents a hydrogen atom or a $C_1$ to $C_{10}$ hydrocarbon group optionally comprising one to three heteroatoms; X represents an amino acid, a peptide, a carbohydrate moiety or a $OR^2$ wherein $R^2$ represents a hydrogen atom or a $C_1$ to $C_{20}$ hydrocarbon group optionally comprising one to three heteroatoms and n is 0 when the dotted line represents a single bond or n is 1 when the dotted line represents no bond; comprising treating the precursor compound to form 2-acetyl-1-pyrroline.

A second object of the present invention is use of a compound of formula (I) as defined above to release 2-acetyl-1-pyrrolidine.

A third object of the present invention is method to confer, enhance, improve or modify the flavor properties of a flavoring composition or of a flavored article, comprising adding to the composition or article an effective amount of at least one compound of formula (I) as defined above.

Another object of the present invention is a method for intensifying or prolonging the diffusion effect of the characteristic flavor of 2-acetyl-1-pyrrolidine by exposing the precursor compound of formula (I) as define above to a temperature above 30° C.

Another object of the present invention is a compound of formula

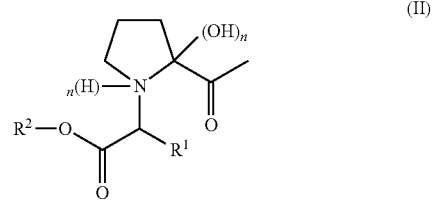

(II)

in the form of any one of its stereoisomers, tautomers, salts or as a mixture thereof, and wherein $R^1$ represents a hydrogen atom or a $C_1$ to $C_3$ alkyl group optionally substituted by a carboxylic acid or an phenyl group; $R^2$ represents a hydrogen atom or a $C_1$ to $C_6$ hydrocarbon group and n is 0 when the dotted line represents a single bond or n is 1 when the dotted line represents no bond provided that 2-(2-acetylpyrrolidin-1-yl)acetic acid, 2-(2-acetylpyrrolidin-1-yl)butanoic acid, ethyl 2-(2-acetylpyrrolidin-1-yl)propanoate, methyl 2-(2-acetylpyrrolidin-1-yl)acetate are excluded.

Another object of the present invention is a flavoring composition comprising:
i. One or more compound of formula (I) as defined above;
ii. at least one ingredient selected from the group consisting of a flavor carrier, a flavoring co-ingredient and a mixture thereof; and
iii. optionally, at least one flavor adjuvant.

A last object of the present invention is a flavored consumer product comprising a compound as defined above or a composition as defined above.

BRIEF DESCRIPTION OF THE DRAWINGS

FIG. 1: Analysis of the concentration of 2-acetylpyrroline in function of time.

DESCRIPTION OF THE INVENTION

Surprisingly, it has now been discovered that a compound of formula (I) is a precursor to the highly valuable volatile compound 2-acetyl-1-pyrroline facilitating the use of 2-AP in flavored consumer product.

So, the first object of the present invention is a method to release 2-acetyl-1-pyrroline from a precursor compound of formula

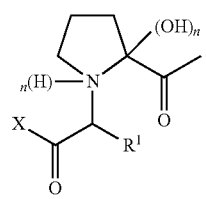

in the form of any one of its stereoisomers, tautomers, salts or as a mixture thereof, and wherein $R^1$ represents a hydrogen atom or a $C_1$ to $C_{10}$ hydrocarbon group optionally comprising one to three heteroatoms; X represents an amino acid, a peptide, a carbohydrate moiety or a $OR^2$ wherein $R^2$ represents a hydrogen atom or a $C_1$ to $C_{20}$ hydrocarbon group optionally comprising one to three heteroatoms and n is 0 when the dotted line represents a single bond or n is 1 when the dotted line represents no bond.

Said method comprises treating the precursor compound to form 2-acetyl-1-pyrroline.

For the sake of clarity, by the expression "any one of its stereoisomers", or the similar, it is meant the normal meaning understood by a person skilled in the art, i.e. that the invention compound can be a pure or be in the form of a mixture of enantiomers or diastereomers.

By the term "tautomers", or the similar, it is meant the normal meaning understood by a person skilled in the art, i.e. that the ketone may be in a form of an enol.

By the term "salts", or the similar, it is meant the normal meaning understood by a person skilled in the art, i.e. that compound of formula (I) in presence of an acid such as HCl, sulfuric acid, phosphoric acid or hydrogeno sulfates, reacts with said acid to form the corresponding salt.

By the term "amino acid", it is meant the normal meaning in the art; i.e. a compound having a carboxylic functional group and an amine functional group. The amino acid may be natural or synthetic. Preferably, the amino acid may be a natural alpha amino acid.

The term "peptide" designates compound composed of at least two amino acids connected by peptide bonds. The peptides may be an oligopeptide comprising from 2 to twenty amino acids or a polypeptides comprising more than twenty peptides.

By the term "a carbohydrate moiety", or the similar, it is meant the normal meaning understood by a person skilled in the art, i.e. a monosaccharide, an oligosaccharide or a polysaccharide.

The term "hydrocarbon group" is understood as a group consisting of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynyl group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of the type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of the topologies or being saturated or unsaturated, as explained above. Similarly, in all the embodiments of the invention, when a group is mentioned as being in the form of one type of saturation or unsaturation, (e.g. alkyl), it is meant that the group can be in any type of topology (e.g. linear, cyclic or branched) or having several moieties with various topologies. In all the embodiments of the invention, when it is mentioned that the hydrocarbon group may optionally comprises heteroatom such as oxygen atoms, nitrogen atoms or sulphur atoms, it is meant that at least one hydrogen atom of the hydrocarbon group may be substituted by a heteroatom and/or that carbon atom of the hydrocarbon chain may be substituted/replaced by a heteroatom; i.e. the hydrocarbon may comprise as substituent or, as part of the chain, functional group such as ether, thiol, amine, ester, amide.

The expression "the dotted line represents no bond" is understood that compound of formula (I) does not comprise ring. In other words; when n is 0 and the dotted line represents a single bond, the precursor compound is of formula

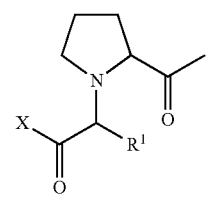

in the form of any one of its stereoisomers, tautomers, salts or as a mixture thereof, and wherein $R^1$ and $R^2$ has the same meaning as defined above.

and when n is 1 and the dotted line represents no bond, the precursor compound is of formula

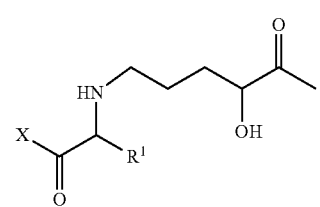

in the form of any one of its stereoisomers, tautomers, salts or as a mixture thereof, and wherein $R^1$ and $R^2$ has the same meaning as defined above.

Preferably, the precursor compound is a compound of formula (I'). In other words, n is 0 and the dotted line is a single bond.

According to any embodiments of the inventions, X may represent a $OR^2$ wherein $R^2$ represents a hydrogen atom or a $C_1$ to $C_{20}$ hydrocarbon group optionally comprising one to three heteroatoms.

According to any embodiments of the inventions, the precursor compound is of formula

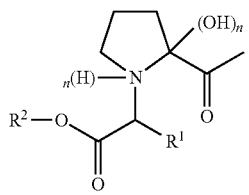

(II)

in the form of any one of its stereoisomers, tautomers, salts or as a mixture thereof, and wherein $R^1$, $R^2$, n and the dotted line have the same meaning as define above.

According to any embodiments of the inventions, $R^1$ may represent a hydrogen atom or a $C_1$ to $C_{10}$ hydrocarbon group optionally comprising one to three oxygen, nitrogen or sulfur atoms. Preferably, $R^1$ may represent a hydrogen atom or a $C_1$ to $C_4$ alkyl group optionally substituted by a carboxylic acid, an amide, a thiol, a $C_{1-3}$ thioether, an amine, a hydroxyl, an imidazolyl, and indolyl, a phenyl or a hydroxyphenyl group.

Preferably, $R^1$ may represent a hydrogen atom, a $C_1$ to $C_3$ alkyl group optionally substituted by a carboxylic acid or a phenyl group. Preferably, $R^1$ may represent a hydrogen atom, a methyl group, an ethyl group, a propyl group, an isopropyl group, a $(CH_2)_p COOH$ group wherein p is 1 or 2 or a benzyl group. Preferably, $R^1$ may represent a hydrogen atom, a methyl group, a $(CH_2)_p COOH$ group wherein p is 1 or 2 or a benzyl group. Preferably, $R^1$ may represent a hydrogen atom, a methyl group or a $(CH_2)_p COOH$ group wherein p is 1 or 2. Even more preferably, $R^1$ may represent a hydrogen atom or a methyl group.

According to any one of the invention's embodiments, $R^2$ may represent a hydrogen atom or $C_1$ to $C_{10}$ hydrocarbon group optionally comprising one to three oxygen, nitrogen, sulfur or halogen atoms. Preferably, $R^2$ may represent a hydrogen atom or $C_1$ to $C_6$ hydrocarbon group optionally comprising one to three oxygen, nitrogen or sulfur atoms. Preferably, $R^2$ may represent a hydrogen atom or a $C_1$ to $C_3$ hydrocarbon group. Preferably, $R^2$ may represent a hydrogen atom or a $C_1$ to $C_3$ alkyl group. Preferably, $R^2$ may represent a hydrogen atom or a $C_1$ to $C_3$ linear alkyl group. Even more preferably, $R^2$ may represent a hydrogen atom.

According to any one of the above embodiments of the invention, said compounds (I) are $C_8$-$C_{23}$ compounds, preferably $C_8$-$C_{15}$ compounds.

According to any embodiments of the inventions, the precursor compound may be selected from the group consisting of (4-hydroxy-5-oxohexyl)glycine, 2-(2-acetylpyrrolidin-1-yl)acetic acid, (4-hydroxy-5-oxohexyl)alanine, 2-(2-acetylpyrrolidin-1-yl)propionic acid, methyl (4-hydroxy-5-oxohexyl)alaninate, methyl 2-(2-acetylpyrrolidin-1-yl)propanoate, (4-hydroxy-5-oxohexyl)phenylalanine, 2-(2-acetylpyrrolidin-1-yl)-3-phenylpropanoic acid, (4-hydroxy-5-oxohexyl)aspartic acid, 2-(2-acetylpyrrolidin-1-yl)succinic acid, (4-hydroxy-5-oxohexyl)glutamic acid and 2-(2-acetylpyrrolidin-1-yl)-5-oxohexanoic acid. Preferably, the precursor compound may be selected from the group consisting of 2-(2-acetylpyrrolidin-1-yl)acetic acid, 2-(2-acetylpyrrolidin-1-yl)propionic acid, methyl 2-(2-acetylpyrrolidin-1-yl)propanoate, 2-(2-acetylpyrrolidin-1-yl)-3-phenylpropanoic acid, 2-(2-acetylpyrrolidin-1-yl)succinic acid and 2-(2-acetylpyrrolidin-1-yl)-5-oxohexanoic acid.

According to any embodiments of the inventions, the release of 2-acetyl-1-pyrrolidine occurs by exposing the precursor compound to a temperature above 30° C., even more, above 50° C., even more, above 60° C., even more, above 70° C., even more, above 80° C., even more, above 90° C.

The precursor compound of formula (I) has never been reported in the literature. So another object of the present invention is a compound of formula

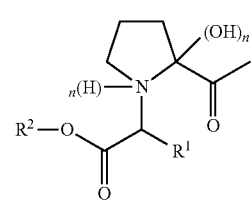

(II)

in the form of any one of its stereoisomers, tautomers, salts or as a mixture thereof, and wherein $R^1$ represents a hydrogen atom or a $C_1$ to $C_3$ alkyl group optionally substituted by a carboxylic acid or an phenyl group; $R^2$ represents a hydrogen atom or a $C_1$ to $C_6$ hydrocarbon group and n is 0 when the dotted line represents a single bond or n is 1 when the dotted line represents no bond provided that 2-(2-acetylpyrrolidin-1-yl)acetic acid, 2-(2-acetylpyrrolidin-1-yl)butanoic acid, ethyl 2-(2-acetylpyrrolidin-1-yl)propanoate, methyl 2-(2-acetylpyrrolidin-1-yl)acetate are excluded.

Another object of the present invention is a method for intensifying or prolonging the diffusion effect of the characteristic flavor of 2-acetyl-1-pyrrolidine by exposing the precursor compound of formula (I) as define above to a temperature above 30° C. even more, above 50° C., even more, above 60° C., even more, above 70° C., even more, above 80° C., even more, above 90° C.

Another object of the present invention is the use of a compound of formula (I) as defined above to release 2-acetyl-1-pyrrolidine. In other words, it concerns confer, enhance, improve or modify the flavor properties of a flavoring composition or of a flavored article, comprising adding to the composition or article an effective amount of at least one compound of formula (I) as defined above, e.g. to impart its typical note. Understood that the final hedonic effect may depend on the precise dosage and on the organoleptic properties of the invention's compound, but anyway the addition of the invention's compound will impart to the final product its typical touch in the form of a note, touch or aspect depending on the dosage.

By "use of a compound of formula (I)" it has to be understood here also the use of any composition containing a compound (I) and which can be advantageously employed in the flavor industry.

Said compositions, which in fact can be advantageously employed as flavoring ingredients, are also an object of the present invention.

Therefore, the present invention also relates to a flavoring composition comprising:
i. at least a precursor compound, as defined above;
ii. at least one ingredient selected from the group consisting of a flavor carrier, a flavoring co-ingredient and a mixture thereof; and
iii. optionally at least one flavor adjuvant.

The term "flavor carrier" designates a material which is substantially neutral from a flavor point of view, insofar as it does not significantly alter the organoleptic properties of flavoring ingredients. The carrier may be a liquid or a solid.

Suitable liquid carriers include, for instance, an emulsifying system, i.e. a solvent and a surfactant system, or a solvent commonly used in flavors. A detailed description of the nature and type of solvents commonly used in flavor cannot be exhaustive. Suitable solvents used in flavor include, for instance, propylene glycol, triacetine, caprylic/capric triglyceride (Neobee®), triethyl citrate, benzylic alcohol, ethanol, vegetable oils such as Linseed oil, sunflower oil or coconut oil, glycerol Suitable solid carriers include, for instance, absorbing gums or polymers, or even encapsulating materials. Examples of such materials may comprise wall-forming and plasticizing materials, such as mono, di- or polysaccharides, natural or modified starches, hydrocolloids, cellulose derivatives, polyvinyl acetates, polyvinylalcohols, xanthan gum, arabic gum, acacia gum or yet the materials cited in reference texts such as H. Scherz, Hydrokolloid: Stabilisatoren, Dickungs- and Geliermittel in Lebensmitteln, Band 2 der Schriftenreihe Lebensmittelchemie, Lebensmittelqualitat, Behr's VerlagGmbH & Co., Hamburg, 1996. Encapsulation is a well-known process to a person skilled in the art, and may be performed, for instance, using techniques such as spray-drying, agglomeration, extrusion, coating, plating, coacervation and the like.

By "flavoring or perfuming co-ingredient" it is meant here a compound, which is used in flavoring or perfuming preparations or compositions to impart a hedonic effect. In other words such an ingredient, to be considered as being a flavoring or perfuming one, must be recognized by a person skilled in the art as being able to impart or modify in a positive or pleasant way the taste or the odor of a composition, and not just as having a taste or an odor.

The nature and type of the flavoring or perfuming co-ingredients present in the composition do not warrant a more detailed description here, the skilled person being able to select them on the basis of its general knowledge and according to intended use or application and the desired organoleptic effect. In general terms, these flavoring or perfuming co-ingredients belong to chemical classes as varied as alcohols, aldehydes, ketones, esters, ethers, acetates, nitriles, terpenoids, nitrogenous or sulphurous heterocyclic compounds and essential oils, and said flavoring or perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of flavor and perfumery. It is also understood that said co-ingredients may also be compounds known to release in a controlled manner various types of flavoring or perfuming compounds.

By "flavor adjuvant", it is meant here an ingredient capable of imparting additional added benefit such as a color (e.g. caramel), chemical stability, and so on. A detailed description of the nature and type of adjuvant commonly used in flavoring compositions cannot be exhaustive. Nevertheless, such adjuvants are well known to a person skilled in the art who will be able to select them on the basis of its general knowledge and according to intended use or application. One may cite as specific non-limiting examples the following: viscosity agents (e.g. emulsifier, thickeners, gelling and/or rheology modifiers, e.g. pectin or agar gum), stabilizing agents (e.g. antioxidant, heat/light and or buffers agents e.g. citric acid), coloring agents (e.g. natural or synthetic or natural extract imparting color), preservatives (e.g. antibacterial or antimicrobial or antifungal agents, e.g. benzoic acid), vitamins and mixtures thereof.

According to any one of the above embodiments, the flavored composition may further comprise ingredient imparting a warming, a tingling, a salivating, a cleaning or an alcohol enhancement effect such as capsicum extract, spice extract (e.g. ginger, maniguette, all types of peppers including Sichuan, piperine, capsaicine, jambu extract, spilanthol.

It is understood that a person skilled in the art is perfectly able to design optimal formulations for the desired effect by admixing the above mentioned components of a flavoring or perfuming composition, simply by applying the standard knowledge of the art as well as by trial and error methodologies.

For the sake of clarity, it is also understood that any mixture resulting directly from a chemical synthesis, e.g. a reaction medium without an adequate purification, in which the compounds of the invention would be involved as a starting, intermediate or end-product could not be considered as a flavoring or perfuming composition according to the invention as far as said mixture does not provide the inventive compound in a suitable form for perfumery or for flavor. Thus, unpurified reaction mixtures are generally excluded from the present invention unless otherwise specified.

A composition consisting of at least one invention's precursor and at least one flavor carrier represents a particular embodiment of the invention as well as a flavoring composition comprising at least one invention's precursor, at least one flavor carrier, at least one flavor co-ingredient, and optionally at least one flavor adjuvant.

Furthermore, the invention's precursor can be advantageously used in all the fields of flavor to positively impart or modify the taste of a consumer product into which said precursor is added. Consequently, the present invention relates to a flavored consumer product comprising the invention's precursor or the invention's composition as defined above.

For the sake of clarity, by "flavored consumer product" it is meant to designate an edible product or oral composition such as, for example, pharmaceutical compositions, edible gel mixes and compositions, dental compositions, foodstuffs beverages and beverage products. The flavored consumer product may be in a different form. A non-exhaustive list of suitable form of the consumer product may include fried, frozen, marinated, battered, chilled, dehydrated, powder blended, canned, reconstituted, retorted, baked, cooked, fermented, microfiltred, pasteurized, blended or preserved. Therefore, a flavored consumer product according to the invention comprises the invention's composition, as well as optional benefit agents, corresponding to taste and flavor profile of the desired edible product, e.g. a cream dessert. The nature and type of the constituents of the foodstuffs or beverages do not warrant a more detailed description here, the skilled person being able to select them on the basis of his general knowledge and according to the nature of said product.

Typical examples of said flavored consumer product include:
   Baked goods (e.g. breads, dry biscuits, cakes, rice cakes, rice crackers, cookies, crackers, donuts, muffins, pastries, pre-mixes, other baked goods), Non-alcoholic beverages (e.g. aqueous beverages, enhanced/slightly sweetened water drinks, flavored carbonated and still mineral and table waters, carbonated soft drinks, non-carbonated beverages, carbonated waters, still waters, softs, bottled waters, sports/energy drinks, juice drinks, vegetable juices, vegetable juice preparations, broth drinks), Alcoholic beverages (e.g. beer and malt beverages, spirituous beverages, wines, liquors), Instant or ready-to-drink beverages (e.g. instant vegetable drinks, powdered soft drinks, instant coffees and teas, black teas, green teas, oolong teas, herbal infusions, cacaos (e.g. water-based), tea-based drinks, coffee-based drinks, cacao-based drinks, infusions, syrups, frozen fruits, frozen fruit juices, water-based ices, fruit ices, sorbets), Cereal products (e.g. breakfast cereals, cereal bars, energy bars/nutritional bars, granolas, pre-cooked ready-made rice products, rice flour products, millet and sorghum products, raw or pre-cooked noodles and pasta products), Dairy based products (e.g. fruit or flavored yoghurts, ice creams, fruit ices, frozen desserts, fresh cheeses, soft cheeses, hard cheeses, milk drinks, wheys, butters, partially or wholly hydrolysed milk protein-containing products, fermented milk products, condensed milks and analogues)

Dairy analogues (imitation dairy products) containing non-dairy ingredients (plant-based proteins, vegetable fats), Confectionary products (e.g. filings, toppings, chewing gums, hard and soft candies), Chocolate and compound coatings (e.g. chocolates, spreads), Products based on fat and oil or emulsions thereof (e.g. mayonnaises, spreads, regular or low fat margarines, butter/margarine blends, flavored oils, shortenings, remoulades, dressings, salad dressings, spice preparations, peanut butters), Eggs or egg products (dried eggs, egg whites, egg yolks, custards), Desserts (e.g. gelatins, puddings, dessert creams), Products made of soya protein or other soya bean fractions (e.g. soya milk and products made therefrom, soya lecithin-containing preparations, fermented products such as tofu or tempeh or products manufactured therefrom, soya sauces), Vegetable preparations (e.g. ketchups, sauces, processed and reconstituted vegetables, dried vegetables, deep frozen vegetables, pre-cooked vegetables, vegetables pickled in vinegar, vegetable concentrates or pastes, cooked vegetables, potato preparations), Fruit preparations (e.g. jams, marmalades, canned fruits)

Vegetarian meat analogues or meat replacers, vegetarian burgers

Spices or spice preparations (e.g. mustard preparations, horseradish preparations, pickles), spice mixtures and, in particular seasonings which are used, for example, in the field of snacks.

Snack articles (e.g. baked or fried potato crisps or potato dough products, bread dough products, extrudates based on maize, rice or ground nuts), Ready dishes (e.g. instant noodles, rice, pastas, pizzas, tortillas, wraps) and soups and broths (e.g. stock, savory cubes, dried soups, instant soups, pre-cooked soups, retorted soups), sauces (instant sauces, dried sauces, ready-made sauces, gravies, sweet sauces, a relish sauces, a sour sauces), oral care product, such as toothpastes, mouth washes, dental care products (e.g. denture adhesives), dental rinsing, mouth sprays, dental powders, dental gels or dental floss, pet or animal food.

Preferably, the flavored consumer product may be baked goods, dairy based products, dairy analogues, products based on fat and oil or emulsions thereof, milk products, confectionary products, desserts, chocolate and compound coatings, cereal products, non-alcoholic beverages, alcoholic beverages or instant or ready-to-drink beverages.

Preferably, the flavored consumer product may be covertures and filling, products based on sugars, breads, dry biscuits, cakes, rice cakes, rice crackers, cookies, crackers, donuts, muffins, pastries, pre-mixes, filings, toppings, fruit or flavored yoghurts, ice creams, fruit ices, frozen desserts, spreads, regular or low fat margarines, butter/margarine blends, flavored oils, shortenings, dressings, spice preparations, peanut butters, fresh cheeses, soft cheeses, milk drinks, wheys, butters, partially or wholly hydrolysed milk protein-containing products, fermented milk products, condensed milk and analogues, gelatins, puddings, dessert creams, chocolates, spreads, aqueous beverages, enhanced/slightly sweetened water drinks, flavored carbonated and still mineral and table waters, carbonated soft drinks, non-carbonated beverages, carbonated waters, still waters, softs, bottled waters, sports/energy drinks, juice drinks, vegetable juices, vegetable juice preparations, beer and malt beverages, spirituous beverages, wines, liquors, instant vegetable drinks, powdered soft drinks, instant coffees and teas, black teas, green teas, oolong teas, herbal infusions, cacaos, tea-based drinks, coffee-based drinks, cacao-based drinks, infusions, syrups, chewing gums, hard and soft candies, frozen fruits, frozen fruit juices, water-based ices, fruit ices, sorbets, breakfast cereals, cereal bars, energy bars/nutritional bars, granolas, pre-cooked ready-made rice products, rice flour products, millet and sorghum products, raw or pre-cooked noodles and pasta products.

Some of the above-mentioned flavored consumer products may represent an aggressive medium for the invention's precursor, so that it may be necessary to protect the invention's composition from premature decomposition, for example by encapsulation.

According to any embodiment of the invention, the pH of the consumer product in which the invention's precursor is introduced is neutral.

The proportions in which the compounds according to the invention can be incorporated into the various aforementioned products or compositions vary within a wide range of values. These values are dependent on the nature of the article to be flavored and on the desired organoleptic effect as well as on the nature of the co-ingredients in a given base when the compounds according to the invention are mixed with flavoring co-ingredients, solvents or additives commonly used in the art.

For example, in the case of flavoring compositions, typical concentrations are in the order of 0.1 ppm to 1000 ppm by weight, preferably of 1 ppm to 100 ppm or even more, of the compounds of the invention based on the weight of the composition into which they are incorporated. In the case of flavored consumer product, typical concentrations are in the order of 0.01 ppm to 100 ppm by weight, preferably of 0.1 ppm to 10 ppm by weight or even more, of the compounds of the invention based on the weight of the consumer product into which they are incorporated.

The invention's precursor can be prepared according to standard method known in the art as described herein-below or may be extracted from plant comprising such an extract as Chinese lettuce. The invention's precursor may also be in a form of an extract, in particular in a form of a Chinese lettuce extract.

EXAMPLES

The invention will now be described in further detail by way of the following examples, wherein the abbreviations have the usual meaning in the art, the temperatures are indicated in degrees centigrade (° C.). NMR spectra were recorded on a Bruker Avance-600 spectrometer (Geneva, Switzerland) at 600.34 MHz for $^1$H and 150.96 MHz for $^{13}$C. The different solvents used were $CDCl_3$, MeOD with tetramethylsilane as internal standard (v=0 ppm) and $D_2O$ with 0.01 M DCl and 3-(trimethylsilyl) propionic acid $d_4$ sodium salt as internal standard (v=0 ppm). δ-chemical shifts were recorded relative to the different internal standards. The Liquid chromatography mass spectrometry were recorded on a Thermo Scientific™ Vanquish™ UHPLC. The mass spectrometer: Thermo Scientific™ Q Exactive™ Basic Mass Spectrometer. A column was an Acquity UPLC BEH C18 1.7 um. 2.1 mm internal diameter×100 mm. Eluent was water/formic acid 0.1% 100% at 0 min to 1 min. then from 1 min 0% to 100% acetonitrile containing 0.1% formic acid at 0.3 mL/min. Another column was Acquity UPLC BEH Amide 1.7 um. 2.1 mm, internal diameter×100 mm. This column was operated with a buffer: solvent A: water/acetonitrile 1/1 containing ammonium formiat 10 mM and formic acid 0.02%, solvent B: water/acetonitrile 1/9 containing ammonium formiat 10 mM and formic acid 0.02% at 0.6 mL 7 min. Gradient started at 100% B for 1 min. then to 85% B in 5 min, to 50% B in 4 min, 20% B in 2 min 0% B in 1 min, then back to 100% B in one min. total run 14 min. This column was also operated in formic acid at 0.3 mL/min flow rate. Solvent A: water containing 0.1% formic acid; solvent B: acetonitrile containing 0.1% formic acid. Gradient started at 90% B to 88% B in 3 min. then to 73% B in 10 min. 63% B in 5 min, 45% B in 2 min and 10% B in 5 min. total run 25 min. MS had targeted SIM in positive mode, with an isolation window of 4.0 m/z and a resolution of 70'000 and max IT of 200 ms. PRM with a resolution of 17'500, max IT 60 ms, isolation window 1.0 m/z and the collision energy 10, 30, 45 was automatically set. The inclusion list was: 172.0967, 190.1072, 186.1124, 204.1228, 230.1021, 248.1127, 244.1178, 262.1284.

Example 1

Preparation of Compounds of Formula (I)

a) Preparation of 4,5-dioxohexanal

2-Methylcyclopent-2-en-1-one (9 g, 93 mol) in $CH_2Cl_2$ (250 mL) was cooled with dry ice and isopropanol at −78° C. in a dedicated ozonolysis flask. Ozone was bubbled through (3.8 g/h) for 80 min (5 g, 102 mol). The gas at the outlet was bubbled in a trap containing KI saturated solution. When the KI solution turned dark, N2 was then bubbled through the reaction mixture to flush out excess ozone. Dimethyl sulfide (DMSO) (27 mL) was added and the mixture was slowly warmed at 22° C. for 3 h. The organic phase was washed with brine, dried on $Na_2SO_4$, and then concentrated to 25 mL. The 4,5-dioxohexanal was kept at −18° C. For the reactions, the solvent was removed just prior to use.

$^{13}$C NMR (150 MHz, DMSO): d 23.4 (q), 27.8 (t), 36.7 (t), 196.5 (s), 197.2 (s), 201.9 (d).

$^1$H NMR (600 MHz, DMSO): δ 2.24 (s, 3H), 2.70 (m, 2H), 2.95 (t, 6.6 Hz, 2H), 9.66 (t, 0.7 Hz, 1H).

b) Preparation of Compound of Formula (I)—General Procedure

The amino acid (8.4 mol) was solubilized in water (10 mL) and $NaHCO_3$ for pH=8. 4,5-Dioxohexanal (8.4 mol) was diluted in MeOH (15 mL) at 22° C. and added to the amino acid. Then $NaBH_3CN$ (0.18 g, 2.8 mol) was added. After 30 min, HCl 1M was added to consume the hydride. MeOH was then removed under vacuum. The crude product was immediately chromatographed on $SiO_2$-RP18 in water to remove all salts, and the fractions were acidified to pH 3 before lyophilization. Chemical yields based on the amino-acids were between 18-25% and purities of pyrrolidine derivatives between 80-90%.

2-(2-acetylpyrrolidin-1-yl)acetic acid

Starting from glycine, a mixture comprising (4-hydroxy-5-oxohexyl)glycine and 2-(2-acetylpyrrolidin-1-yl)acetic acid was obtained and was analyzed with LC-MS (full MS) providing the following peaks: at 0.99 min, (4-hydroxy-5-oxohexyl)glycine ($C_8H_{15}NO_4$, M+H=190.1068) and at 1.10 min, 2-(2-acetylpyrrolidin-1-yl)acetic acid ($C_8H_{13}NO_3$, M+H=172.0968). The crude mixture was purified by chromatography provided 2-(2-acetylpyrrolidin-1-yl)acetic acid in 26% yield.

2-(2-acetylpyrrolidin-1-yl)acetic acid $^{13}$C NMR (150 MHz, MeOD): δ 24.1 (t), 26.7 (q), 28.8 (t), 56.9 (t), 58.9 (t), 74.6 (d), 170.3 (s), 203.6 (s).

$^1$H NMR (600 MHz, MeOD): δ 1.93-2.13 (m, 2H), 2.07-2.53 (m, 2H), 2.30 (s, 3H), 3.22-3.76 (m, 2H), 3.68-3.80 (d, 15.8 Hz, 2H), 4.57 (dd, 6.0 Hz, 9.5 Hz, 1H).

2-(2-acetylpyrrolidin-1-yl)propanoic acid

Starting from alanine, a mixture comprising (4-hydroxy-5-oxohexyl)alanine and 2-(2-acetylpyrrolidin-1-yl)propionic acid was obtained and was analyzed with LC-MS (full MS) providing the following peaks: at 1.13 min, (4-hydroxy-5-oxohexyl)alanine ($C_9H_{17}NO_4$, M+H=204.1230) and at 1.13 min, 2-(2-acetylpyrrolidin-1-yl)propionic acid ($C_9H_{15}NO_3$, M+H=186.1125). The crude mixture was purified by chromatography provided 2-(2-acetylpyrrolidin-1-yl)propionic acid in 25% yield in a form of a mixture of two diastereoisomers.

$^{13}$C NMR (150 MHz, $D_2O$): d 15.3 (q), 26.0 (t), 28.9 (q), 31.6 (t), 57.0 (t), 65.0 (d), 73.6 (d), 175.1 (s), 208.0 (s).

$^1$H NMR (600 MHz, $D_2O$): d 1.57 (d, 7.8 Hz, 3H), 1.88-2.19 (m, 2H), 2.20-2.52 (m, 2H), 2.37 (s, 3H), 3.47-3.79 (m, 2H), 4.22 (m, 1H), 4.91 (dd, 4.8 Hz, 9.6 Hz, 1H).

$^{13}$C NMR (150 MHz, $D_2O$): d 16.3 (q), 26.1 (t), 29.0 (q), 30.7 (t), 56.5 (t), 66.5 (d), 76.2 (d), 175.4 (s), 208.0 (s).

$^1$H NMR (600 MHz, $D_2O$): d 1.50 (d, 7.6 Hz, 3H), 1.88-2.17 (m, 2H), 2.19-2.54 (m, 2H), 2.34 (s, 3H), 3.38-3.78 (m, 2H), 4.20 (m, 1H), 4.77 (m, 1H).

methyl 2-(2-acetylpyrrolidin-1-yl)propanoate

Starting from alanine methyl ester, a mixture comprising methyl (4-hydroxy-5-oxohexyl)alaninate and methyl 2-(2-acetylpyrrolidin-1-yl)propanoate was obtained and was analyzed with LC-MS (full MS) providing the following peaks:

at 1.14 min, one diastereoisomers of 2-(2-acetylpyrrolidin-1-yl)propanoate ($C_{10}H_{17}NO_3$, M+H: 200.1278); at 1.14 min, methyl (4-hydroxy-5-oxohexyl)alaninate ($C_{10}H_{19}NO_4$, M+H=218.1383) and at 1.28 min, another diastereoisomer of 2-(2-acetylpyrrolidin-1-yl)propanoate ($C_{10}H_{17}NO_3$, M+H=200.1278). The crude mixture was purified by chromatography provided methyl 2-(2-acetylpyrrolidin-1-yl) propanoate in 20% yield in a form of a mixture of two diastereoisomers.

$^{13}$C NMR (150 MHz, MeOD): δ 13.9 (q), 24.4 (t), 26.6 (q), 29.1 (t), 53.9 (q), 55.0 (t), 63.2 (d), 74.1 (d), 170.6 (s), 203.2 (s).

$^1$H NMR (600 MHz, MeOD): δ 1.60 (d, 7.14 Hz, 3H), 2.35 (s, 3H), 1.88-2.18 (m, 2H), 2.17-2.58 (m, 2H), 3.44-3.74 (m, 2H), 3.82 (s, 3H), 4.46 (q, 7.14 Hz, 1H), 4.85 (m, 1H).

$^{13}$C NMR (150 MHz, MeOD): δ 13.2 (q), 24.3 (t), 26.6 (q), 29.9 (t), 54.0 (q), 54.5 (t), 61.9 (d), 72.5 (d), 170.4 (s), 203.2 (s).

$^1$H NMR (600 MHz, MeOD): δ 1.64 (d, 7.3 Hz, 3H), 2.33 (s, 3H), 1.88-2.18 (m, 2H), 2.17-2.54 (m, 2H), 3.53-3.74 (m, 2H), 3.82 (s, 3H), 4.40 (q, 7.3 Hz, 1H), 4.96 (m, 1H).

2-(2-acetylpyrrolidin-1-yl)-3-phenylpropanoic acid

Starting from phenylalanine, a mixture comprising (4-hydroxy-5-oxohexyl)phenylalanine and 2-(2-acetylpyrrolidin-1-yl)-3-phenylpropanoic acid was obtained and was analyzed with LC-MS (full MS) providing the following peaks: at 4.14 min, (4-hydroxy-5-oxohexyl)phenylalanine ($C_{15}H_{21}NO_4$, M+H=280.1538); at 4.28, one diastereoisomers of 2-(2-acetylpyrrolidin-1-yl)-3-phenylpropanoic acid ($C_{15}H_{19}NO_3$, M+H=262.1435) and 4.36 min, another diastereoisomers of 2-(2-acetylpyrrolidin-1-yl)-3-phenylpropanoic acid ($C_{15}H_{19}NO_3$, M+H=262.1435). The crude mixture was purified by chromatography provided 2-(2-acetylpyrrolidin-1-yl)-3-phenylpropanoic acid in 22% yield in a form of a mixture of two diastereoisomers.

$^{13}$C NMR (150 MHz, MeOD): (major diastereoisomer) 24.5 (t), 26.3 (q), 29.7 (t), 37.0 (t), 52.8 (t), 69.1 (d), 73.0 (d), 128.2 (d), (129.8, 129.8, 130.3, 130.3 (4d), 172.5 (s), 206.6 (s).

$^1$H NMR (600 MHz, MeOD): δ 1.85-2.10 (m, 2H), 1.98-2.44 (m, 2H), 2.12 (s, 3H), 3.10-3.27 (m, 2H), 3.48-3.53 (m, 2H), 3.97 (t, 7.3 Hz, 1H), 4.52 (dd, 2.1 Hz, 9.3 Hz, 1H), 7.25 (m, 1H), 7.32 (m, 4H).

2-(2-acetylpyrrolidin-1-yl)pentanedioic acid

Starting from glutamic acid, a mixture comprising (4-hydroxy-5-oxohexyl)glutamic acid and 2-(2-acetylpyrrolidin-1-yl)pentanedioic acid was obtained and was analyzed with LC-MS (full MS) providing the following peaks: at 1.11 min, (4-hydroxy-5-oxohexyl)glutamic acid ($C_{11}H_{19}NO_6$, M+H=262.144) and 1.11 min, 2-(2-acetylpyrrolidin-1-yl)pentanedioic acid ($C_{11}H_{17}NO_5$, M+H=244.1340). The crude mixture was purified by chromatography provided 2-(2-acetylpyrrolidin-1-yl)pentanedioic acid in 25% yield.

$^{13}$C NMR (150 MHz, MeOD), major diastereoisomer: 24.5 (t), 27.0 (q), 25.9 (t) 29.4 (t), 34.7 (t), 55.3 (t), 72.0 (d), 173.4 (s), 180.9 (s), 205.4 (s).

$^1$H NMR (600 MHz, MeOD): δ 1.85-2.15 (m, 2H), 2.01-2.11 (m, 2H), 2.03-2.40 (m, 2H), 2.30 (s, 3H), 2.42 (m, 2H), 3.20-3.82 (m, 2H), 3.79 (m, 1H), 4.52 (dd, 3.4 Hz, 10.3 Hz, 1H).

Example 2

Thermal Release of 2-acetylpyrroline 10 mg of 2-(2-acetylpyrrolidin-1-yl)propanoic acid prepared in example 1 was dissolved in water (2 mL) containing 5 mg NaHCO$_3$ and heated for 60 min at 120° C. in a heating block. The release kinetics was measured as mentioned below.

A calibrations curve was done with water (6 mL), 10 μL of toluene and lutidine (50 μL of a solution 1 mg/mL EtOH), then vial 1 to 4 contained respectively, instead of toluene, 2-AP in toluene, respectively 10 μL of 50, 100, 500, 1000 μg/mL. All measurements were made in triplicate. The SPME conditions were: 5 min. conditioning at 270° C., the exposure was 3 min after having heated the sample at 120° C. during 15 min and then 60 min. The thermo-desorption, in split less mode, was 1.5 min at 250° C. The quantification was performed in full MS based on the intensity ratio in extract ion mode: 111 (2-AP)/107 (lutidine). The pH was in any case between 6.5-7.0. The standard error was ±16%.

The release of 2-acetylpyrroline from 2-(2-acetylpyrrolidin-1-yl)propanoic acid was shown in FIG. 1.

The invention claimed is:

1. A compound of formula

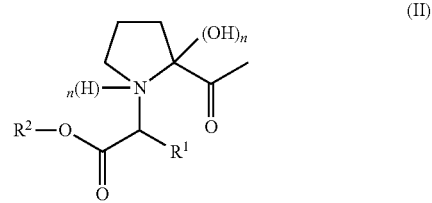

(II)

in the form of any one of its stereoisomers, tautomers, salts or as a mixture thereof,
wherein
the dotted line represents a single bond or no bond;
R$^1$ represents a hydrogen atom or a C$_1$ to C$_3$ alkyl group optionally substituted by a carboxylic acid or a phenyl group;
R$^2$ represents a hydrogen atom or a C$_1$ to C$_6$ hydrocarbon group; and
n is 0 when the dotted line represents a single bond or n is 1 when the dotted line represents no bond;
provided that 2-(2-acetylpyrrolidin-1-yl) acetic acid, 2-(2-acetylpyrrolidin-1-yl) butanoic acid, ethyl 2-(2-acetylpyrrolidin-1-yl) propanoate, methyl 2-(2-acetylpyrrolidin-1-yl) acetate, and 2-(2-acetylpyrrolidin-1-yl) propionic acid, and their stereoisomers, tautomers, and salts are excluded.

2. A flavoring composition comprising:
i. One or more compound of formula (II) as defined in claim 1;
ii. at least one ingredient selected from the group consisting of a flavor carrier, a flavoring co-ingredient and a mixture thereof; and
iii. optionally, at least one flavor adjuvant.

3. A flavored consumer product comprising a compound as defined in claim 1.

4. The flavored consumer product according to claim 3, wherein the flavored consumer product is selected from the group consisting of baked goods, dairy based products, dairy analogues, products based on fat and oil or emulsions thereof, milk products, confectionary products, desserts, chocolate and compound coatings, cereal products, non-alcoholic beverages, alcoholic beverages, instant beverages, and ready-to-drink beverages.

5. The flavored consumer product according to claim 4, wherein the flavored consumer product is selected from the group consisting of covertures and filling, products based on sugars, breads, dry biscuits, cakes, rice cakes, rice crackers, cookies, crackers, donuts, muffins, pastries, pre-mixes, fillings, toppings, fruit or flavored yoghurts, ice creams, fruit ices, frozen desserts, spreads, regular or low fat margarines, butter/margarine blends, flavored oils, shortenings, dressings, spice preparations, peanut butters, fresh cheeses, soft cheeses, milk drinks, wheys, butters, partially or wholly hydrolysed milk protein-containing products, fermented milk products, condensed milk and analogues, gelatins, puddings, dessert creams, chocolates, spreads, aqueous beverages, enhanced/slightly sweetened water drinks, flavored carbonated and still mineral and table waters, carbonated soft drinks, non-carbonated beverages, carbonated waters, still waters, softs, bottled waters, sports/energy drinks, juice drinks, vegetable juices, vegetable juice preparations, beer and malt beverages, spirituous beverages, wines, liquors, instant vegetable drinks, powdered soft drinks, instant coffees and teas, black teas, green teas, oolong teas, herbal infusions, cacaos, tea-based drinks, coffee-based drinks, cacao-based drinks, infusions, syrups, chewing gums, hard and soft candies, frozen fruits, frozen fruit juices, water-based ices, fruit ices, sorbets, breakfast cereals, cereal bars, energy bars/nutritional bars, granolas, pre-cooked ready-made rice products, rice flour products, millet and sorghum products, raw or pre-cooked noodles and pasta products.

6. A flavored consumer product comprising a composition as defined in claim 2.

7. The flavored consumer product according to claim 6, wherein the flavored consumer product is selected from the group consisting of baked goods, dairy based products, dairy analogues, products based on fat and oil or emulsions thereof, milk products, confectionary products, desserts, chocolate and compound coatings, cereal products, non-alcoholic beverages, alcoholic beverages, instant beverages, and ready-to-drink beverages.

8. The flavored consumer product according to claim 7, wherein the flavored consumer product is selected from the group consisting of covertures and filling, products based on sugars, breads, dry biscuits, cakes, rice cakes, rice crackers, cookies, crackers, donuts, muffins, pastries, pre-mixes, fillings, toppings, fruit or flavored yoghurts, ice creams, fruit ices, frozen desserts, spreads, regular or low fat margarines, butter/margarine blends, flavored oils, shortenings, dressings, spice preparations, peanut butters, fresh cheeses, soft cheeses, milk drinks, wheys, butters, partially or wholly hydrolysed milk protein-containing products, fermented milk products, condensed milk and analogues, gelatins, puddings, dessert creams, chocolates, spreads, aqueous beverages, enhanced/slightly sweetened water drinks, flavored carbonated and still mineral and table waters, carbonated soft drinks, non-carbonated beverages, carbonated waters, still waters, softs, bottled waters, sports/energy drinks, juice drinks, vegetable juices, vegetable juice preparations, beer and malt beverages, spirituous beverages, wines, liquors, instant vegetable drinks, powdered soft drinks, instant coffees and teas, black teas, green teas, oolong teas, herbal infusions, cacaos, tea-based drinks, coffee-based drinks, cacao-based drinks, infusions, syrups, chewing gums, hard and soft candies, frozen fruits, frozen fruit juices, water-based ices, fruit ices, sorbets, breakfast cereals, cereal bars, energy bars/nutritional bars, granolas, pre-cooked ready-made rice products, rice flour products, millet and sorghum products, raw or pre-cooked noodles and pasta products.

\* \* \* \* \*